(12) United States Patent
Urvoy et al.

(10) Patent No.: US 11,602,399 B2
(45) Date of Patent: Mar. 14, 2023

(54) SYSTEMS AND METHODS TO ADJUST BONE CUT POSITIONING BASED ON BONE HARDNESS

(71) Applicant: DePuy Ireland Unlimited Company, Ringaskiddy (IE)

(72) Inventors: Francois Urvoy, Sainte Nazaire les Eymes (FR); Robert John Wright, Dedham, MA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 643 days.

(21) Appl. No.: 16/593,586

(22) Filed: Oct. 4, 2019

(65) Prior Publication Data

US 2021/0100629 A1 Apr. 8, 2021

(51) Int. Cl.
*A61B 34/30* (2016.01)
*A61B 17/15* (2006.01)
(Continued)

(52) U.S. Cl.
CPC ............ *A61B 34/30* (2016.02); *A61B 17/155* (2013.01); *A61B 17/157* (2013.01); *A61B 17/88* (2013.01); *A61F 2/28* (2013.01)

(58) Field of Classification Search
CPC ......... A61B 34/30; A61B 34/10; A61B 34/20; A61B 17/14; A61B 17/154; A61B 17/155; A61B 17/157; A61B 17/16
See application file for complete search history.

(56) References Cited

U.S. PATENT DOCUMENTS 9,220,510 B2 12/2015 Cheal et al.
2011/0306985 A1* 12/2011 Inoue .................... A61B 34/30
606/130
(Continued)

FOREIGN PATENT DOCUMENTS

EP 3065651 B1 4/2018
WO 2011/158113 A1 12/2011
(Continued)

OTHER PUBLICATIONS

International Search Report and Written Opinion for Application No. PCT/EP2020/077732, dated Nov. 16, 2020 (19 Pages).
(Continued)

*Primary Examiner* — Samuel S Hanna
(74) *Attorney, Agent, or Firm* — Condo Roccia Koptiw LLP

(57) ABSTRACT

Systems and methods for adjusting bone cut positioning are disclosed that can aid in optimizing implant size selection and positioning relative to bone during, e.g., orthopedic surgical procedures such as knee arthroplasty, hip arthroplasty, etc. In one embodiment, such a surgical method can include performing a first bone cut of a first bone using an at least partially robot-assisted surgical instrument, detecting one or more parameters related to bone hardness, selecting a bone hardness index based on the one or more detected parameters, and adjusting a position of a second bone cut of the first bone based on the selected bone hardness index to optimize implant fit relative to bone. Detecting the one or more parameters related to bone hardness can be performed in a number of manners, including by monitoring energy required to perform the first bone cut.

33 Claims, 11 Drawing Sheets

(51) Int. Cl.
 A61B 17/88 (2006.01)
 A61F 2/28 (2006.01)

(56) References Cited

U.S. PATENT DOCUMENTS

| | | |
|---|---|---|
| 2012/0059378 A1 | 3/2012 | Farrell |
| 2015/0257838 A1 | 9/2015 | Huet et al. |
| 2016/0135816 A1 | 5/2016 | Lavallee et al. |
| 2016/0206376 A1 | 7/2016 | Haider et al. |
| 2016/0270853 A1 | 9/2016 | Lavallee et al. |
| 2016/0274571 A1 | 9/2016 | Lavallee et al. |
| 2016/0279877 A1 | 9/2016 | Lavallee |
| 2018/0085133 A1 | 3/2018 | Lavallee et al. |
| 2018/0280065 A1 | 10/2018 | Babic et al. |
| 2018/0360541 A1 | 12/2018 | Morita et al. |

FOREIGN PATENT DOCUMENTS

| | | |
|---|---|---|
| WO | 2012/024319 A2 | 2/2012 |
| WO | 2012/024323 A2 | 2/2012 |
| WO | 2018/103945 A1 | 6/2018 |
| WO | 2018/104439 A1 | 6/2018 |
| WO | 2018/104523 A1 | 6/2018 |
| WO | 2018/167246 A1 | 9/2018 |

OTHER PUBLICATIONS

Enayati Nima et al., "Haptics in Robot-Assisted Surgery: Challenges and Benefits", IEEE Reviews in Biomedical Engineering, vol. 9, Mar. 3, 2016, pp. 49-65.

* cited by examiner

SYSTEMS AND METHODS TO ADJUST BONE CUT POSITIONING BASED ON BONE HARDNESS

FIELD

This disclosure relates generally to surgical systems and methods, and more particularly to systems and methods for adjusting bone cut positioning based on bone hardness. Such systems and methods can be used in various procedures to optimize implant size selection and positioning relative to bone, including, e.g., robotic or robot-assisted orthopedic surgical procedures such as knee arthroplasty, hip arthroplasty, etc.

BACKGROUND

Various surgical procedures involve the placement of implants within a patient's body. Certain such procedures utilize cementless, or press-fit, implants that rely initially on friction forces from an interference fit, and subsequently on osseointegration after bone growth over time, to fixate the implant relative to the patient's bone. For example, hip arthroplasty procedures can utilize a cementless, or press-fit, prostheses, such as the acetabular cup prosthesis fitted to a patient's pelvis. By way of further example, knee arthroplasty procedures, such as total knee arthroplasty (TKA) and unicompartmental knee arthroplasty (UKA), can involve cutting or drilling a patient's femur and tibia bones to facilitate placement of cementless knee replacement implants. In such procedures, a patient's femur is often cut along a distal end, as well as along an anterior and a posterior surface. The cut surfaces reshape a distal portion of the femur to receive a cementless implant thereon. The planes of the anterior and posterior cuts can be parallel or otherwise angled relative to one another. For parallel planes, A-P is the distance between the two planes, while for angled planes A-P is measured as the closest distance between the two cut surfaces of the bone.

Some prior surgical procedures involve the use of a bone cutting block paired with a given size of implant. The bone cutting block includes fixed slots to guide a cutting instrument in performing the anterior and posterior bone cuts. The internal dimensions of the cementless implant are slightly less than those of the cut femur because the ingrowth surface of a cementless implant is designed for an interference, or press-, fit and is slightly prominent. In certain cases, however, difficulty in placement can arise from variations in bone quality, density, or hardness. For example, it can be difficult to introduce a cementless implant in the case of a patient with hard bone. A surgeon can risk breaking the bone if too much force is exerted to position the implant, or it may not be possible to fully seat the implant. Conversely, an implant placed over a soft bone may not provide sufficient compression force to the bone to achieve solid fixation and promote subsequent osseointegration.

Moreover, variations in bone quality, density, or hardness can influence the precision of bone cuts due to differing effects on a cutting element, such as a blade. This can cause an unintentional increase or decrease in a zone of injury impacted by the cutting element. For example, bone density can affect both vertical and horizontal movements of oscillating cutting blade tools. In more dense bone, for example, a saw blade can deflect during a cut, thereby removing less bone than intended and, in some cases, requiring a second cut in the same plane to remove the desired amount of bone. Conversely, in soft bone the vibration of the saw blade can result in deflection of the blade deeper than the intended plane of the cut.

Variations in bone hardness can be accounted for by adjusting the A-P distance to make the cut femur either larger or smaller in order to increase or reduce compressive forces applied by a cementless implant and to address blade deflection during a cut. This can be done by adjusting a position of one or more of the anterior and posterior bone cuts in the example of a TKA or UKA procedure. Certain prior bone cutting blocks, however, utilize slots having a fixed A-P dimension, thereby precluding any adjustment in this distance to account for bone hardness. Other prior approaches enable such adjustment with, for example, cutting blocks having adjustable slots to vary A-P distance. Such methods can require a surgeon to guess or estimate appropriate variation and rely solely on personal experience of the surgeon in a particular operation. There is a need for improved systems and methods for adjusting bone cut positioning in these and other similar procedures.

Further, computer-assisted surgical (CAS) systems are increasingly utilized to aid surgeons in performing various procedures. Such systems can include any of a robot and a navigation system that can assist in performing a surgery by accurately tracking movement of one or more surgical instruments and/or assisting or controlling movement of one or more surgical instruments in at least one degree of freedom. While bone cutting blocks can be utilized in connection with CAS systems, in some procedures cutting blocks can be eliminated, as a surgical robot can control the positioning of a cutting instrument or constrain a surgeon's movement of the instrument in one or more degrees of freedom and allow each of the anterior and posterior bone cuts to be performed independently.

Accordingly, there is a need for improved systems and methods for adjusting bone cut positioning to account for bone hardness with placing cementless implants during various surgical procedures, especially those involving the use of a CAS system or surgical robot.

SUMMARY

In some embodiments, improved systems and methods for adjusting bone cut positioning are disclosed that can aid in optimizing implant positioning relative to bone during, e.g., orthopedic surgical procedures such as hip arthroplasty, knee arthroplasty, etc. The various systems and methods described herein can utilize computer-assisted surgical systems (CAS) that include at least partially robot-assisted surgical instruments to aid in detecting one or more parameters related to bone hardness. Based on the detected parameters, a bone hardness index can be determined for the patient's bone, and positioning of at least one bone cut can be adjusted based on the selected bone hardness index to optimize fit of an implant relative to the bone. The systems and methods described herein can utilize an algorithmic and/or empirical model that can be tuned based on repeated use to optimize correlation of detected parameters and bone hardness index values. Further, such a model can receive from users inputs to adjust which bone hardness index values correlate with a given set of detected parameters related to bone hardness. Such systems and methods can select an appropriate amount of bone to be removed when preparing for a cementless or press-fit implant to provide sufficient compressive force to softer bone while not overly compressing harder bone in a manner that might cause damage.

In one aspect, a surgical method for adjusting bone cut positioning is disclosed that can include performing a first bone cut of a first bone using an at least partially robot-assisted surgical instrument, detecting one or more parameters related to bone hardness, selecting a bone hardness index based on the one or more detected parameters, and adjusting a position of a second bone cut of the first bone based on the selected bone hardness index to optimize implant fit relative to bone.

The systems and methods described herein can have a number of additional features and/or variations, all of which are within the scope of the present disclosure. In some embodiments, for example, the first bone cut can be a distal cut of a femur during a knee arthroplasty operation. Further, the second bone cut can be any of an anterior and a posterior cut of the femur. In some embodiments, the method can further include placing an implant over the areas of the first and second bone cuts. The implant can be a cementless, press-fit implant in some embodiments.

In certain embodiments, the method can further include measuring a force required to place the implant, and adjusting the bone hardness index based the measured force. In such embodiments, the bone hardness index and any algorithms or empirical models for correlating the detected parameters related to bone hardness with bone hardness index values can be tuned based on actual performance.

In other embodiments, the same general technique can be utilized in other areas of a patient's anatomy for similarly placed implants. By way of example, in some embodiments, the first bone cut can any of create or enlarge a cavity in the first bone. This can be the case, for example, in embodiments in which the first bone is the pelvis, such as during hip arthroplasty procedures. For example, in such embodiments the cavity can be the acetabulum. Moreover, in some embodiments the second bone cut can be a final bone cut that determines a surface configured to contact an implant. The implant can, in some embodiments, be a cementless, press-fit implant.

In some embodiments, the position of the second bone cut can be adjusted to increase an amount of bone removed as the bone hardness index increases and the position of the second bone cut is adjusted to decrease an amount of bone removed as the bone hardness index decreases. This can reduce the compressive forces exerted on the bone by, e.g., a cementless implant when used with harder bone and increase the compressive forces exerted on the bone when used with softer bone.

In some embodiments, selection of the bone hardness index can be received as an input from a user after performing the first bone cut. That is, a user can perform the first bone cut and select the bone hardness index based on their experience performing the first bone cut. In such embodiments, the user can detect the one or more parameters related to bone hardness through, e.g., tactile feedback, audible feedback, speed of cut, etc.

In certain embodiments, a computer-assisted surgical system can perform at least the steps of detecting one or more parameters related to bone hardness and selecting a bone hardness index based on the one or more detected parameters, and the method can further include receiving from a user a correction to the selected bone hardness index. In such embodiments, a user can leverage their experience to correct or adjust a bone hardness index selected by a computer-assisted surgical system. Further, in some embodiments such feedback can be utilized to tune any algorithm or empirical model utilized to correlate detected parameters related to bone hardness with bone hardness index values.

In various embodiments, the timing of detecting one or more parameters related to bone hardness can vary relative to performance of the first bone cut. For example, in some embodiments detecting one or more parameters related to bone hardness can occur while performing the first bone cut. In some embodiments, detecting one or more parameters related to bone hardness can include recording total energy (e.g., work) required by the surgical instrument to perform the first bone cut relative to an area of the first bone cut. In other embodiments, detecting one or more parameters related to bone hardness can include continuously recording instantaneous energy (e.g., force) required by the surgical instrument to perform the first bone cut. In such embodiments, detecting one or more parameters related to bone hardness can further include correlating the recorded instantaneous energy required at each time during the first bone cut with a position of the surgical instrument to map variations in bone hardness over an area of the first bone cut. In some embodiments, selecting a bone hardness index can include discarding recorded bone hardness information for select areas of the first bone cut, such as cortical bone areas.

In another embodiment, detecting one or more parameters related to bone hardness can occur after performing the first bone cut and can include utilizing a robot to advance an instrument into bone exposed by the first bone cut in a direction transverse to a plane of the first bone cut. In such embodiments, detecting one or more parameters related to bone hardness can include recording total energy (e.g., work) required by the robot to advance the instrument. Alternatively, detecting one or more parameters related to bone hardness can include continuously recording instantaneous energy (e.g., force) required by the robot to advance the instrument. The instrument advanced into the bone can be any of the surgical instrument utilized to perform the first bone cut, a surgical drill, a pin, and another surgical instrument.

In certain embodiments, the method can further include drilling at least one pin bore using an at least partially robot-assisted surgical drill and detecting one or more parameters related to bone hardness can occur before performing the first bone cut. In such embodiments, detecting one or more parameters related to bone hardness can include recording total energy (e.g., work) required by the surgical drill to form the at least one pin bore. Alternatively, detecting one or more parameters related to bone hardness can include continuously recording instantaneous energy (e.g., force) required by the surgical drill to form the at least one pin bore. Further, detecting one or more parameters related to bone hardness can further include correlating the recorded instantaneous energy required at each time while forming the at least one pin bore with a position of the surgical drill to map variations in bone hardness over a depth of the at least one pin bore. In some embodiments, selecting a bone hardness index can include discarding recorded bone hardness information for select portions of the at least one pin bore, such as cortical bone areas.

In another aspect, a surgical method for adjusting bone cut positioning is disclosed that can include pre-operatively measuring bone density at a planned surgical site, selecting a bone hardness index based on the pre-operative measurement of bone density, and adjusting a position of a bone cut based on the selected bone hardness index to optimize implant fit relative to bone.

As with the other aspects and embodiments described herein, a number of additional features or variations are possible. For example, in some embodiments pre-operatively measuring bone density can include any of quantitative computed tomography (QCT), dual energy x-ray absorptiometry (DEXA), and biopsy. Further, in some embodiments adjusting the position of a bone cut can include selecting a cutting block having cut slot placement that corresponds to the selected bone hardness index. Moreover, in some embodiments the steps of selecting the bone hardness index and adjusting the position of a bone cut can be performed pre-operatively in surgical planning software.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Figure 1:
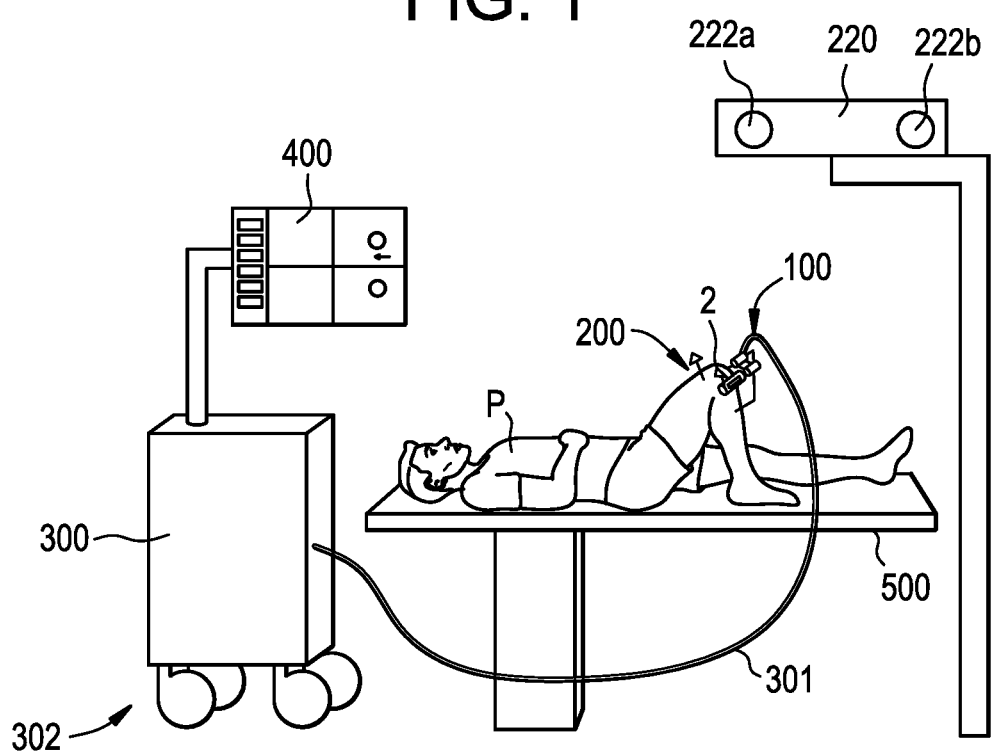
FIG. 1 is an illustration of a surgical system according to the present disclosure.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed systems and methods, such dimensions are not intended to limit the types of shapes that can be used in conjunction with such systems and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the systems, and the components thereof, can depend at least on the anatomy of the subject in which the systems will be used, the size and shape of components with which the devices will be used, and the methods and procedures in which the devices will be used.

FIGS. 1-4 illustrate embodiments of computer-assisted surgical (CAS) systems that can be utilized with the systems and methods described herein. Such systems can utilize any of surgical navigation/tracking and robot control or assistance to monitor or control movement of one or more surgical instruments during a procedure. While the illustrated embodiments and accompanying description make particular reference to knee surgery and, in particular, to total knee arthroplasty (TKA) or unicompartmental knee arthroplasty (UKA), wherein the anatomical structure to be cut is a joint formed of the femur and tibia, the systems and methods described herein are not limited to this application. Rather, the systems and methods described herein can be utilized in various applications involving robotic, robot-assisted, and non-robotic operations where bone cuts are required and adjustment of cut position may be appropriate to optimize implant fit with regard to, for example, bone hardness.

An example of another application is hip arthroplasty where it can be desirable to optimize the fit of an artificial acetabular cup used as a prosthesis in hemi or total hip replacement. The process described here can optimize the size of the acetabulum cavity cut by a robot into the pelvic bone in order to optimize the press fit of the acetabular cup into the acetabulum cavity. The tool used to perform the bone cuts in such an application can be, for example, a reamer or a burr. Such procedures typically involve preparing the cavity by successive enlargements to remove bone from the pelvis. The teachings of the present disclosure can be applied to such a procedure. For example, a bone hardness index (as described in more detail below) can be determined while performing one or more initial resections on the bone, which can be used to adjust the position of a final resection and therefore the shape the final cavity.

FIG. 1 shows an overview of one embodiment of a surgical system according to the present disclosure. Further details of surgical systems that can be utilized in connection with the present disclosure can be found in International Publication Nos. WO 2018/103945; WO 2018/104523; WO 2018/167246; WO 2018/104439; and U.S. Pat. Pub. No. 2016/0135816. The entirety of each of these publications is incorporated by reference herein. Returning to the figure, a patient P is shown lying on an operating table 500, e.g., about to undergo a total knee arthroplasty (TKA). A cutting tool, such as a saw 2, which is intended to cut the tibial and femoral bones along at least one target plane is used by a user, such as a surgeon. The cutting tool is held by the robotic device 100 and is constrained in each target plane by an actuation unit 4 (not shown in FIG. 1, but better seen in subsequent drawings). The robotic device 100 is connected to a control unit 300 that controls the actuation unit. Said control unit typically comprises power supply, AC/DC converters, motion controllers to power the motors of the actuation unit, fuses, real-time control system interface circuits, and other components conventionally included in surgical robot devices. As noted above, the description provided herein makes reference to the surgical system shown in FIG. 1 and the cutting tool 2, but the present disclosure is also contemplated for use with any surgical device having an end effector or tool configured to manipulate tissue. This could be a saw blade, burr, reamer, mill, knife, or any other implement that could cut or deform bone and is appropriate for use in a given operation (e.g., a planar saw may be more appropriate in a knee arthroplasty operation while a rotary burr may be more appropriate in a hip arthroplasty operation, etc.). Further, the present disclosure is also contemplated to include use of such instruments by surgical robots, by users with some degree of robotic assistance, and without involvement of surgical robots or robotic assistance (e.g., where solely surgical navigation/tracking is utilized).

Returning to the system illustrated in FIG. 1, the system also comprises a tracking unit 200, such that the relative pose or three-dimensional position and orientation of the device and the anatomical structure to be cut can be tracked in real time and shared between a real time control unit and a planning system. At least one coordinate system can be attached to the anatomical structure while at least one coordinate system can be attached to the cutting tool and/or the robotic device. The tracking unit can measure the relative motions between both coordinate systems in real time. Real time can, in some embodiments, mean high frequencies greater than twenty Hertz, in some embodiments in the range of one hundred to five hundred Hertz, with low latency, in some embodiments less than five milliseconds.

The tracking unit 200 can utilize any of a variety of trackers and tracking technologies known for use in surgical navigation. These can include, for example, optical trackers consisting of reflective or active markers detected by a sensor disposed inside or in view of the surgical field. In the illustrated embodiment, for example, the tracking unit 200 can include a passive optical tracker consisting of, for example, a constellation of reflective tracking elements having a fixed geometric relationship that can be coupled to a portion of patient anatomy, a surgical instrument, or other component to be tracked. A stereoscopic sensor 220 having two or more physically separated detectors 222a, 222b can be used to detect light reflected off each of the tracking elements (e.g., reflected infra-red (IR) light in some embodiments). The sensor 220, in some embodiments in conjunction with other information processing components such as the control unit 300, can utilize the known fixed geometric relationship between the tracking elements and the detected positions of the tracking elements in the fields of view of the two detectors 222a, 222b to determine a precise three-dimensional position and orientation of the tracker (and therefore of the anatomy or instrument coupled thereto) within the surgical field.

In some embodiments, however, other types of surgical navigation and tracking can be employed in place of, or in addition to, the above-described reflective optical tracking. For example, in some embodiments optical tracking can be employed using active light emitters rather than reflective elements, such as light emitting diodes (LEDs). In other embodiments, electromagnetic trackers can be employed, while in still other embodiments any of inertial sensors using gyroscopic measurements, ultrasonic sensors, radio-frequency identification (RFID) sensors, or other known sensors can be employed.

Regardless of how it is gathered, position and orientation data can be transferred between components (e.g., to the control unit 300) via any suitable connection, e.g., with wires 301 or wirelessly using a low latency transfer protocol. The real-time control unit can carry out real-time control algorithms at a reasonably high frequency with low additional latency to coordinate movement of the robotic device 100.

Figure 2:
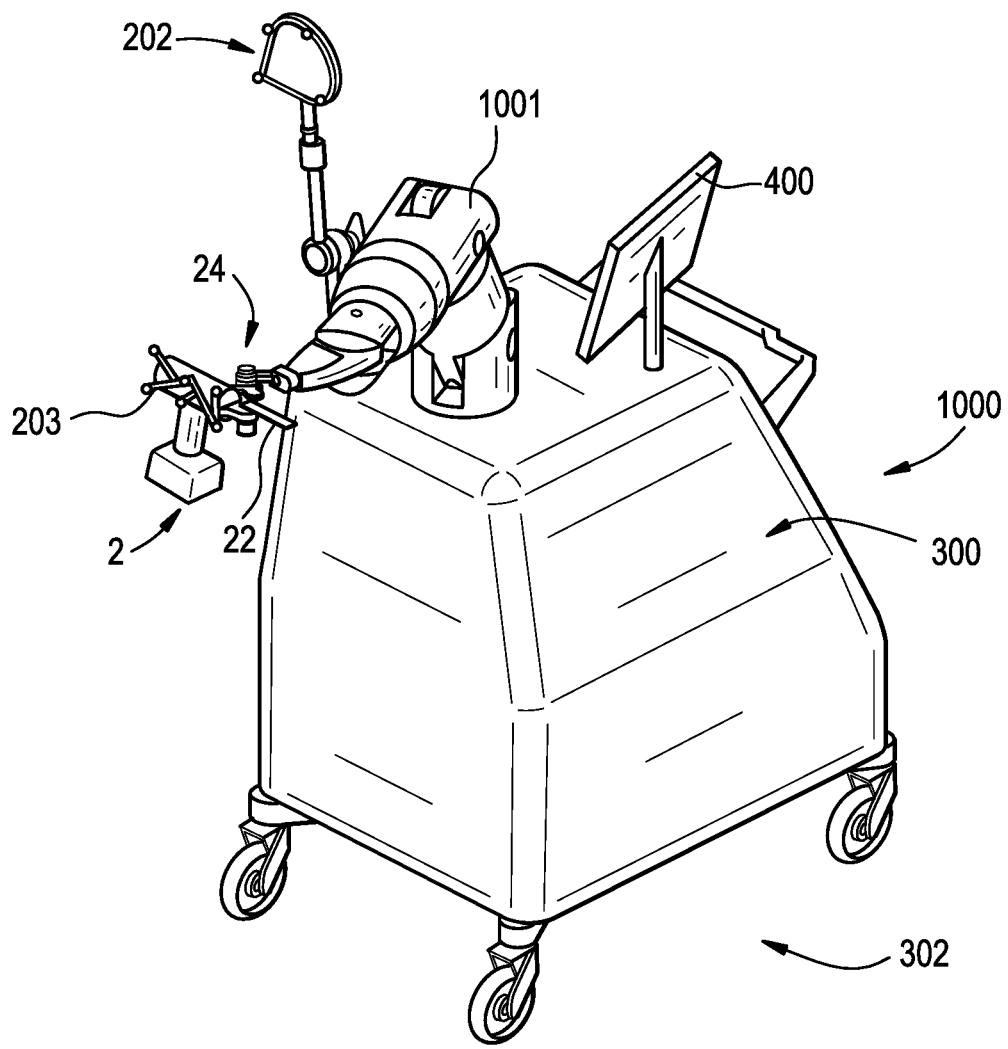
FIG. 2 is an illustration of one embodiment of a surgical robot according to the present disclosure.
Figure 3:
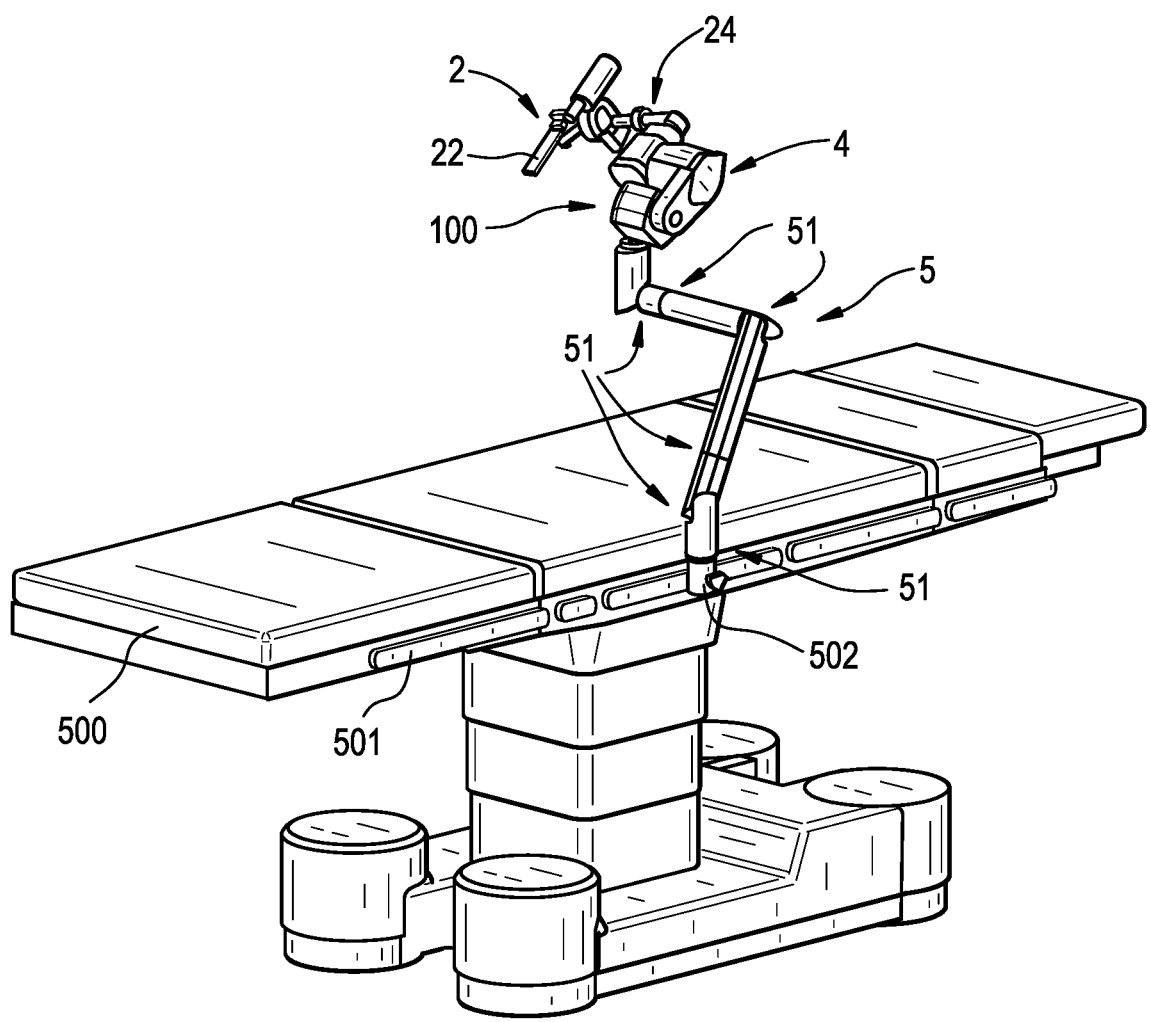
FIG. 3 is an illustration of another embodiment of a surgical robot according to the present disclosure.

FIGS. 2 and 3 illustrate different embodiments of a surgical system. In FIG. 2, for example, an integrated surgical robot 1000 can include the control unit and tracking unit in a cart 302 that can be moved in the operating room. The cart can include an articulating arm 1001 extending from the cart, as well as a holding mechanism 24 to interface the arm 1001 with the cutting tool 2. In some embodiments, however, various components, such as the control unit and tracking unit or components thereof, can be mounted on separate carts. In addition, articulated holding arms, lighting systems, or components of the tracking unit can be mounted directly on the anatomical structure or on some parts attached to the robotic device. For example, the cutting tool can rigidly support an electromagnetic emitter while electromagnetic sensors can be attached to the anatomical structure.

The system can also include a visual user interface 400 that is intended to display feedback information to a user and enable system configuration by the user. The feedback information can include indications regarding cutting planes, patient or instrument positioning, directions to achieved desired positioning, etc. The user interface 400 can include a screen, which can be located on a cart in the operating room, e.g., on the same cart 302 as the control unit and tracking unit, or on a separate cart, or attached to the walls or the celling of the operating room. Moreover, in addition to or instead of a screen, the user interface can include one or more indicators arranged on the robotic device itself to provide information to the user. For example, the indicator(s) can be made of LEDs arranged to indicate arrows, numbers or letters, or a miniature display.

FIG. 3 illustrates an embodiment of a surgical system wherein the robotic device 100 is coupled to a holding arm 5 that is fixed to a rail 501 of an operating table 500 by a clamp 502. In embodiments such as those illustrated in FIG. 3, the robotic device 100 can be coupled (e.g., using wires or wireless connections, etc.) to one or more carts including above-described components, such as the control unit 300, interface 400, etc. The robotic device 100 can include a cutting tool 2 coupled to an actuation unit 4 using a holding mechanism 24, as described herein. The robotic device 100 can in turn be coupled to the holding arm 5. The holding arm 5 shown in FIG. 3 can be made of several articulated segments using ball-and-socket joints, rotational, and/or translational joints. In the illustrated example, the holding arm can be formed of a series of pivot links 51 that can be oriented at 90 degree or other angle offsets from one another to enable movement of the arm in multiple planes.

The robotic device 100 shown in FIG. 3 can also include an actuation unit 4. The actuation unit 4 can have a serial architecture made of a plurality of mobile segments. In some embodiments, the actuation unit can have three motorized rotational degrees of freedom for adjusting the position and orientation of a cutting tool 2 relative to target anatomy. In other embodiments, the actuation unit can have two motorized rotational degrees of freedom and one or two motorized translational degrees of freedom. Generally speaking, the actuation unit can include one or more, and in some embodiments from three to five, motorized degrees of freedom. In some embodiments, at least two of the motorized degrees of freedom can be rotational degrees of freedom orthogonal to each other. In some embodiments, the actuation unit can include three rotational motorized degrees of freedom.

The segments and their components can be integrated in an optimal way such that the robotic device 100 remains as compact and light as possible while remaining strong enough to be able to hold the cutting tool, as well as resist normal pressure applied by the user when he/she manipulates the cutting tool. In some embodiments, the segments of the actuation unit 4 can be arranged such that the rotation axes of two adjacent segments are substantially parallel to each other while axes of segments separated by an intervening segment can be substantially orthogonal to one another. Such an arrangement can provide an advantage in certain procedures, such as a total knee arthroplasty (TKA), where both the tibial cut and the femoral cuts can be made with a single initial position of the robotic device 100.

As shown in FIGS. 2 and 3, in some embodiments the cutting tool can be a surgical saw 2 coupled to the actuation unit 4. The saw 2 can include a saw blade 22 that oscillates in a determined plane (which can be referred to as the "cutting plane"). Thus, the saw blade can be operated to cut an anatomical structure according to a target plane without requiring any cutting block, provided that the actuation unit 4 constrains the saw in the target plane in real time. Usually, the cutting plane is parallel to the longitudinal axis of the saw 2 and the saw blade 22 oscillates on both sides of this axis—such a saw is sometimes known as a "sagittal saw." According to an embodiment, the saw blade can move back and forth along the longitudinal axis of the saw or a housing thereof—such a saw is sometimes known as a "reciprocating saw."

In certain embodiments, other cutting tools can be utilized. For example, according to another embodiment, the cutting tool can be a rotary burr. In some cases, if the burr head is small (e.g., with a diameter of the order of a few millimeters or less), the operation of the burr constrained in a cutting plane can allow for the creation of a planar cut. The burr tip can be spherical or cylindrical in various embodiments. According to still another embodiment, the cutting tool can be a laser with a system to control the depth of penetration of the laser to avoid damaging soft tissues behind the desired target region (e.g., a bone, etc.). According to yet another embodiment, the cutting tool can be a high-pressure water jet or any other device that creates cuts in an anatomical structure.

Figure 4:
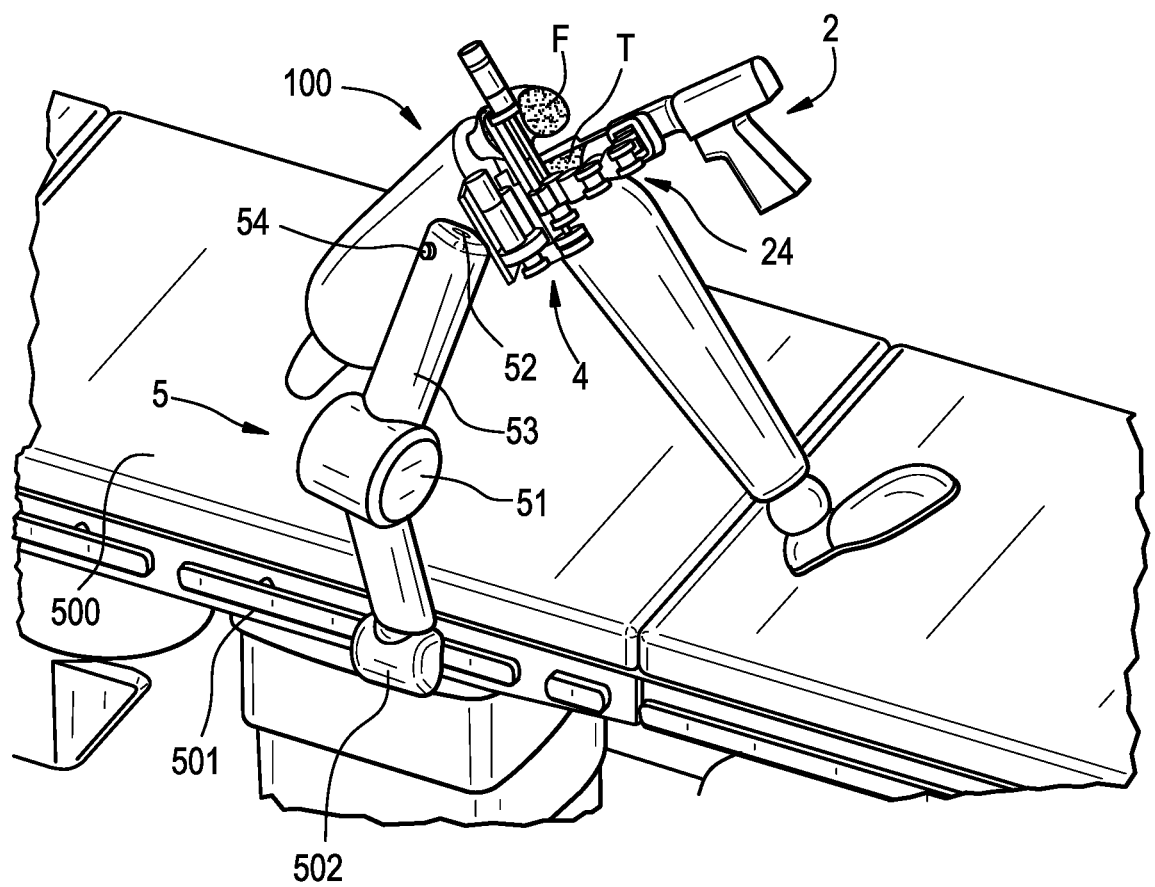
FIG. 4 is an illustration of one embodiment of a setup of the surgical robot of FIG. 3.

FIG. 4 illustrates one embodiment of a setup of the robotic device illustrated in FIG. 3. A patient (only one leg is represented in FIG. 4) is lying on an operating table 500, with the leg in flexed position. Visible in the representative leg of FIG. 4 is the patient's femur F and tibia T. Although not illustrated, the patient's leg can be maintained in a flexed position by wedges, straps, and other implements commonly used in surgical interventions. For example, one wedge can be placed under the foot and another one can be placed on the external side of the hip, in order to reduce inward and outward movements of the flexed leg.

The holding arm 5 can have one end attached to a rail 501 arranged on the operating table 500 and the opposite end attached to the actuation unit 4 of a robotic device 100. The rail to which the holding arm is attached can be the rail located on the same side of the table as the leg of interest, or the rail located on the side of the table opposite to the leg of interest. Any of portions of the patient's anatomy (e.g., the femur F, tibia T, etc.), actuation unit 4, or surgical instrument 2 can include tracking elements (not shown) to enable navigation/tracking of movement of these components during a procedure.

Figure 5:
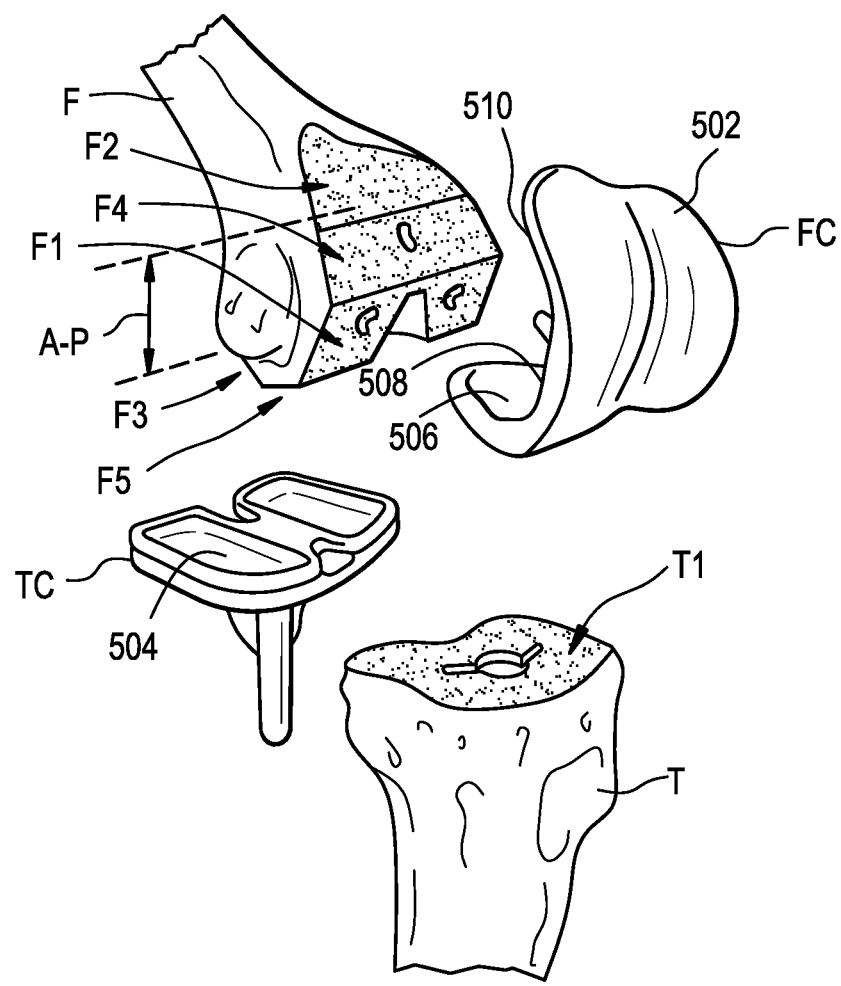
FIG. 5 is an illustration of various bone cuts and cementless implants utilized in one embodiment of a knee arthroplasty procedure.

FIG. 5 is an illustration of a knee and associated cementless, or press-fit, implants and the associated bone cuts required to facilitate placement of the implants during a total knee arthroplasty (TKA) procedure. In the illustrated embodiment, a patient's tibia T is cut at its proximal end and possibly bored down a central axis thereof to facilitate placement of a tibial component (TC) or implant. Also illustrated are cuts that can be formed on a patient's femur (F) to facilitate placement of a femoral component (FC) or implant. Generally, the cuts to be made on the femur F are: a distal cut along plane F1, an anterior cut along plane F2, a posterior cut along plane F3, as well as anterior and posterior chamfers F4, F5 in some embodiments. These additional cuts connect the distal plane and the anterior and posterior planes, respectively.

Turning to the femoral implant FC, it includes a curved outer surface 502 that slides against the upper surface 504 of the tibial implant TC to recreate motion of a natural knee joint. The curved outer surface 502 is opposed by angled planar internal surfaces 506, 508, 510 that abut the posterior, distal, and anterior cut surfaces, respectively. The internal surfaces of the femoral implant FC define a volume that receives the distal end portion of the femur F. As noted above, the volume defined by the femoral implant FC can be slightly smaller than the cut distal portion of the femur F to provide an interference fit and enable cementless implantation. A primary method for varying the amount of interference between the femoral implant FC and the femur F is to adjust a distance A-P between the anterior and posterior cut surfaces of the femur. Note that the plane F2 of the anterior cut and the plane F3 of the posterior cut can be parallel in some embodiments and can be otherwise angled relative to one another in other embodiments. In embodiments where the planes are not parallel with one another, the distance A-P can be measured between the two closest points of the cut surfaces.

Figure 6:
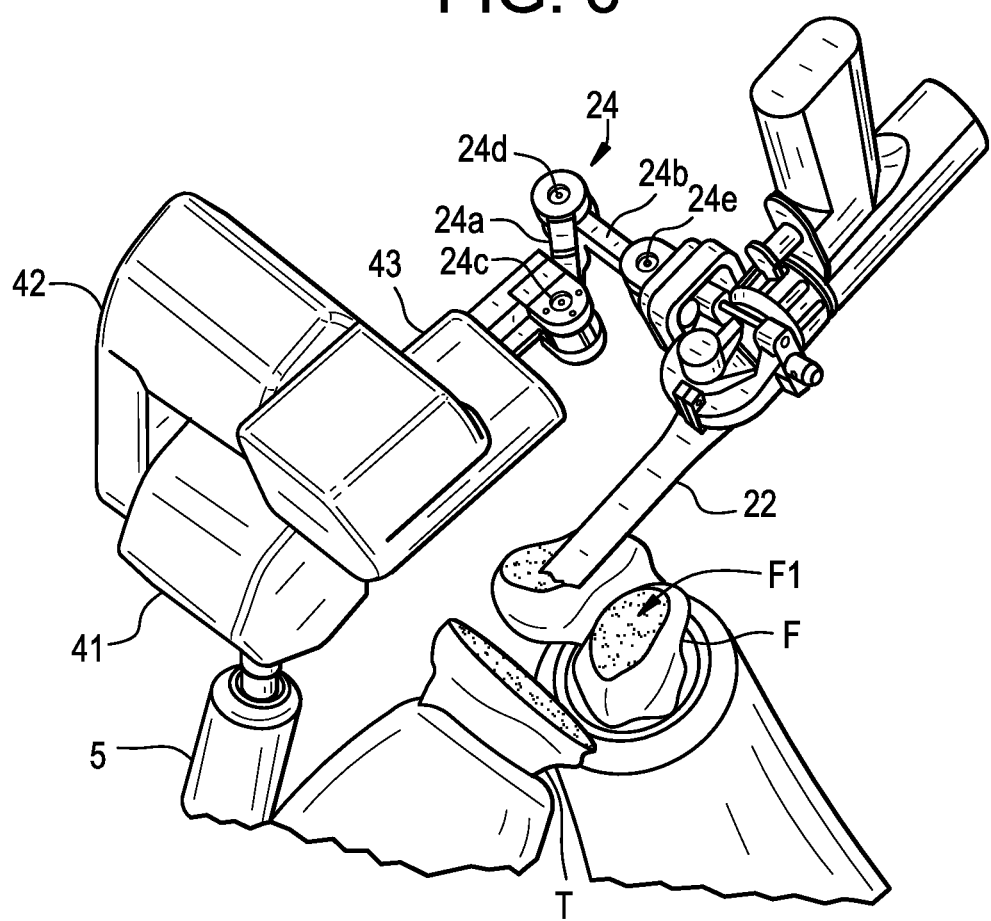
FIG. 6 is an illustration of the surgical robot of FIG. 3 performing a distal bone cut of a patient's femur.
Figure 7:
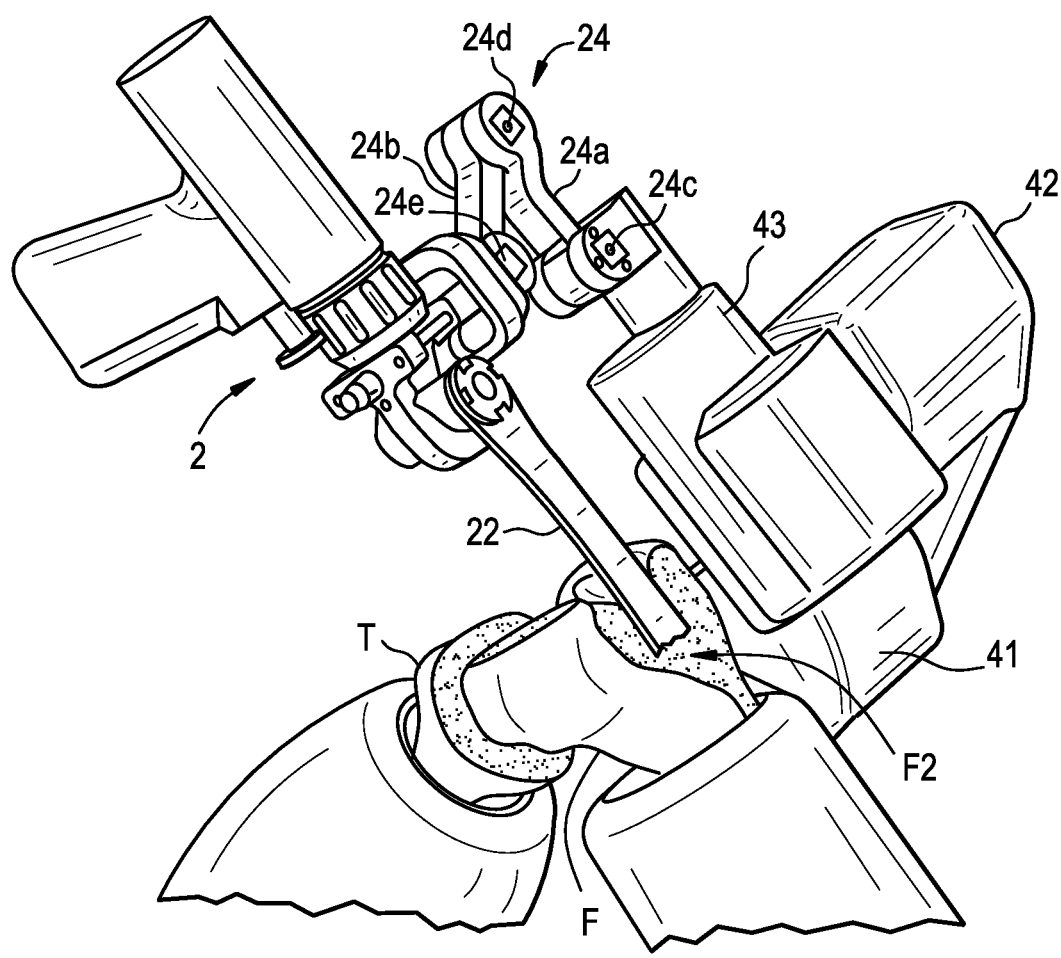
FIG. 7 is an illustration of the surgical robot of FIG. 3 performing an anterior bone cut of a patient's femur.
Figure 8:
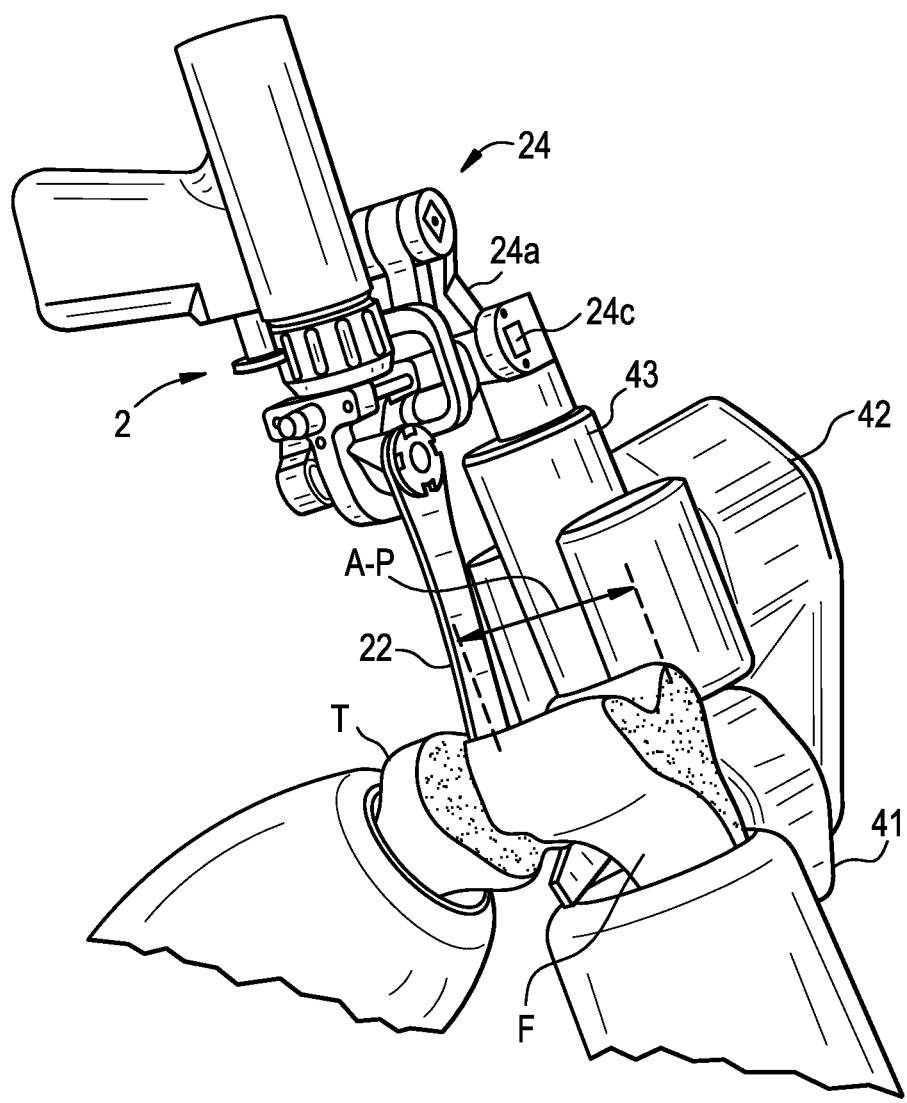
FIG. 8 is an illustration of the surgical robot of FIG. 3 performing a posterior bone cut of a patient's femur.

FIGS. 6-8 illustrate one embodiment of the surgical robot of FIG. 3 performing the various femur bone cuts typically used in a TKA procedure. The distal cut along plane F1 is typically performed first, as shown in FIG. 6. Note that FIG. 6 illustrates the tibial cut complete as well, but the tibia can be processed independently of the femur so this may not be the case in some embodiments. For example, in unicompartmental knee replacement (UKA), the tibia is cut first. Accordingly, when referring to "first" and "second" bone cuts below, note that reference is with respect to first and second cuts of a particular bone, e.g., the femur, and need not include cuts to other bones (e.g., the tibia) that can be completed either before or after the described "first" and "second" bone cuts (e.g., a "first" bone cut described below may not actually be the absolute first bone cut performed during a procedure). FIG. 7 illustrates performance of an anterior bone cut of the femur. As noted, this can be done following the distal bone cut in some embodiments. Finally, FIG. 8 illustrates performance of a posterior bone cut of the femur. Note that order of cutting operation can be varied in different embodiments, especially with respect to which of the anterior and posterior cuts is performed first, but also with respect to any other cut as well.

FIG. 8 provides an alternative illustration of the A-P distance between the anterior and posterior cut surfaces of the femur. As noted above, the internal dimensions of the implant are smaller than the cut distal portion of the femur to provide an interference fit between the femur and the cementless implant FC. The interference fit can provide fixation of the implant relative to the femur and encourage subsequent osseointegration over time. Bone hardness can impact placement of the implant FC, however. For example, in some embodiments a given A-P distance can prove too large for use with patients having hard bone, as the implant cannot be placed over the cut distal portion of the femur or exertion of sufficient force to place the implant can cause fracturing of the bone. Conversely, in some embodiments the given A-P distance can prove too small for use with patients having soft bone, as the implant does not exert sufficient compressive force on the bone to provide required levels of immediate fixation and to promote subsequent osseointegration. Accordingly, it can be desirable to adjust the A-P distance based on bone hardness to provide an optimal implant fit relative to bone. For example, it can be desirable to increase an amount of bone removed for patients having harder bone (e.g., decreasing the A-P distance between the anterior and posterior cut surfaces). This produces a cut distal portion of bone that is smaller to provide additional clearance for fitting the implant thereon (i.e., ensures smooth and full seating of implant without any bone breakage). Conversely, it can be desirable to decrease an amount of bone removed for patients having softer bone (e.g., increasing the A-P distance between the anterior and posterior cut surfaces). This produces a cut distal portion of bone that is larger to provide reduced clearance for fitting the implant thereon (i.e., provides most compressive force and optimal promotion of osseointegration).

It can also be desirable to adjust A-P distance or otherwise adjust cutting element positioning to account for expected blade deflection based on bone hardness or density. This is because, as mentioned above, variation in bone quality, density, or hardness can unintentionally expand or contract a zone of injury impacted by the cutting element. For example, a saw blade can deflect to a shallower trajectory than intended when cutting through harder bone, such that less bone than intended is removed. This can, in some cases, require a second cut in the same plane as a first cut to remove the desired amount of bone. And, conversely, in softer bone a saw blade can deflect to a deeper trajectory than intended, such that more bone is removed than intended. Adjustment of cut positioning based on detected bone hardness can help increase the precision and accuracy of the cuts during a procedure, thereby optimizing implant fit relative to bone.

Figure 9:
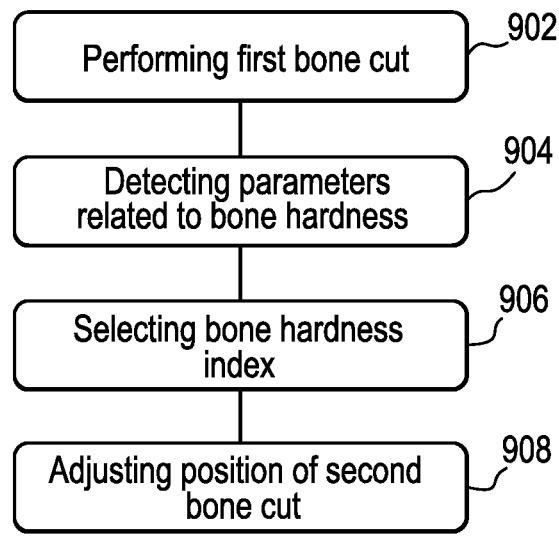
FIG. 9 is a flowchart of one embodiment of a method of adjusting bone cut positioning according to the present disclosure.

The systems and methods disclosed herein utilize capabilities of CAS systems, including surgical robots that assist or control movement of surgical instruments, to detect one or more parameters related to bone hardness, select a bone hardness index based on the one or more detected parameters, and adjust a position of one or more bone cuts based on the selected bone hardness index to optimize implant fit relative to bone. FIG. 9 illustrates one embodiment of a method according to the present disclosure. The method generally includes the steps of performing a first bone cut 902, detecting parameters related to bone hardness 904, selecting a bone hardness index value 906, and adjusting a position of a second bone cut 908 based on the selected bone hardness index. The adjustment can account for desired variations in cut dimensions to facilitate desired interference fitting of an implant based on bone hardness, as well as expected variations in cut dimensions based on expected blade deflection when cutting bone of the selected hardness. A number of additional features and variations are also possible.

For example, in some embodiments the first bone cut can be a distal cut of a femur during a knee arthroplasty operation, i.e., the distal cut along plane F1 shown in FIGS. 5 and 6. The second bone cut can be any of an anterior and posterior cut of the femur, i.e., the cuts along planes F2 and F3 shown in FIGS. 5, 7, and 8, respectively.

The relative timing of performance of the method steps can vary in different embodiments. For example, in some embodiments, detecting one or more parameters related to bone hardness can occur while performing the first bone cut. For example, in some embodiments a user can directly detect one or more parameters related to bone hardness while performing the first bone cut. A user might, for example, detect parameters such as speed of cut, amount of force required to advance cut, or other tactile, visual, or auditory feedback experienced while making the first cut. In such embodiments, a user can provide their own judgment as to how hard bone is based on the one or more parameters detected. As a result, in some embodiments selection of a bone hardness index can be received as an input from a user after performing the first bone cut in some embodiments. A user can provide such an input using, e.g., a keyboard or other input device coupled to a user interface that is part of a CAS system (e.g., as part of interface 400 coupled to controller 300).

The bone hardness index can be, for example, a number on a scale or spectrum that relates to a patient's bone hardness. For example, a bone hardness index might be a value from 1 to 5, where 5 indicates hardest bone, 1 indicates softest bone, and 2-4 indicate degrees in between. The bone hardness index can be related to adjustments in A-P distance for a particular size of implant using an empirical model or algorithm formed from training data and/or ongoing usage. Note that in embodiments where ongoing uses refine the empirical model or algorithm, data can be shared among various CAS systems to aggregate data and provide the best possible tuning. Methods for implementing empirical models or algorithms are not covered in depth in this disclosure. A simple example can include instantiating an empirical model using a base set of training data that indicates appropriate A-P values for various bone hardness index values and/or associates bone hardness index values with values of parameters related to bone hardness. The model can operate based on the training data alone without further adjustment in some embodiments or, in other embodiments, can continue adding usage data to the training data set to fine tune the A-P values associated with each bone hardness index value and/or the parameter values associated with each bone hardness index value, as described in more detail below.

One advantage of utilizing a CAS system, including a system employing at least partial robotic assistance or control of a surgical instrument is that the system can provide quantitative detection of parameters related to bone hardness beyond a surgeon's experienced feedback. For example, in some embodiments detecting one or more parameters related to bone hardness can include recording total energy (e.g., work) required by a surgical instrument (e.g., an oscillating saw) to perform the first bone cut relative to an area of the first bone cut. The energy consumed internally by the cutting system (e.g., energy to put the saw into motion), can be subtracted from the total consumption in order to estimate the energy used to cut the bone only. The bone cut area can be calculated in some embodiments based on the geometry to the implant (e.g., based on the areas of the internal surfaces 506, 508, 510 that abut against the cut surfaces of the bone).

In such embodiments, the CAS system can perform the steps of detecting the one or more parameters related to bone hardness and selecting the bone hardness index value. For example, the total energy/area ratio can lead to selection of a bone hardness index value based on an empirical model wherein the ratio increases as bone hardness increases. In some embodiments, the CAS system can also determine adjustments to the second bone cut, e.g., adjustments to the A-P distance, based on the selected bone hardness index. The relation between the bone hardness index and bone cut adjustments can similarly be set by designers of the system or be continually updated by a system that learns as surgeons enter manual adjustments to the preset values, etc., as described in more detail below.

Alternatively, the CAS system can detect one or more parameters related to bone hardness by continuously recording instantaneous energy (e.g., force) required by the surgical instrument to perform the first bone cut. This can be done, for example, based on detection of instantaneous electrical current draw or intensity required by the surgical instrument at each time during first bone cut. As with the total energy embodiment mentioned above, internal energy consumption within the surgical instrument can be subtracted to provide only energy required to cut bone. The recorded energy at each time during the first bone cut can be correlated with a position of the surgical instrument at each time during the first bone cut to map variations in bone hardness over an area of the first bone cut. That is, the CAS system typically includes a tracking system that can precisely monitor the position of the surgical instrument throughout the first bone cut, and the position tracking can be matched against the energy consumption to provide an illustration of bone hardness across the cut surface. Such a map of energy consumption can be utilized to fine tune the information provided by the total energy solution described above. For example, in some embodiments the data can be analyzed for non-homogeneity, or by selecting the hardness index based only on certain areas while excluding others. In some embodiments, for example, it may be desirable to exclude bone hardness information associated with cortical bone when selecting a bone hardness index value. Using the presently described embodiment, bone hardness information for areas known to be cortical bone can be omitted when selecting a bone hardness index value. Alternatively, a determination of bone hardness index could be made solely based on parameters related to hardness of cortical bone, if desired.

In some embodiments, detecting one or more parameters related to bone hardness can occur after performing a first bone cut. For example, in some embodiments detecting one or more parameters related to bone hardness can include advancing an instrument into bone exposed by the first bone cut. The instrument advanced into the bone can be any of the surgical instrument utilized to perform the first bone cut (e.g., an oscillating saw blade or portion thereof), a surgical drill, a pin, and another surgical instrument.

In some embodiments, the CAS system, including a robot, can be utilized to advance the instrument into bone exposed by the first bone cut. Turning to the example of a TKA procedure, this can be done, for example, by advancing a tool (e.g., the saw blade, another part of the cutting tool, a pin, or other type of specialty indenting instrument coupled to the robot) into the freshly-exposed distal femur bone in a direction transverse to the plane F1 of the first, distal bone cut. As with the example above, the total energy required by the robot to advance the instrument into the exposed bone can be recorded and a bone hardness index value can be selected based on an empirical model or algorithm based on the required total energy. Also similarly to the above-described examples, in other embodiments detecting one or more parameters related to bone hardness can include continuously recording instantaneous energy required by the robot to advance the instrument into the exposed bone. Both methods can permit estimation of the hardness of the bone exposed by the first bone cut (e.g., the distal cut in the example of a TKA procedure).

Figure 10:
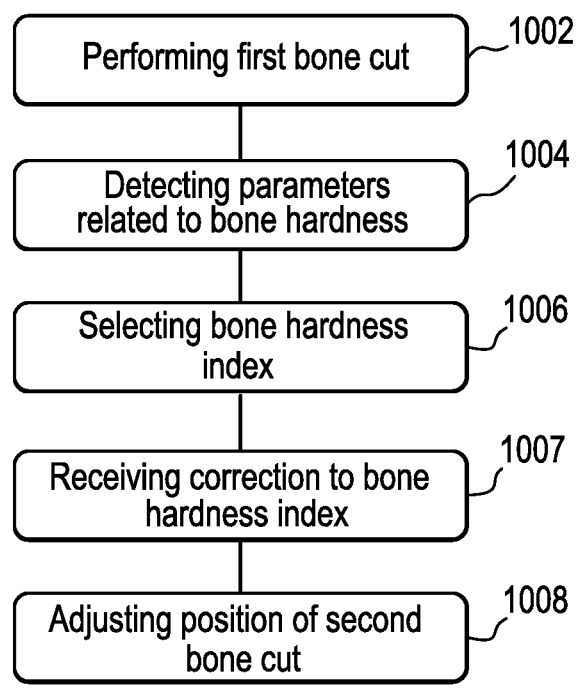
FIG. 10 is a flowchart of another embodiment of a method of adjusting bone cut positioning including receiving a correction to a selected bone hardness index.

The empirical models that link the energy consumption to the bone hardness index can be developed using an expert system algorithm, where the CAS system (more particularly, individual systems and/or several CAS systems sharing information) can "learning by doing" based on, e.g., an initial training data set that is refined over time. Refinement of the model can in some embodiments come in the form of user corrections to model- or CAS system-based selections of bone hardness index values. FIG. 10 illustrates one embodiment of a flowchart of a method including receiving a correction to a bone hardness index selection from a user (1007, other labelled steps similar to those shown in prior figures). The correction can be received from a user, e.g., a surgeon, via a user interface, as described above. Such systems can improve the accuracy of the empirical models used to select the bone hardness index based on a particular set of detected parameters related to bone hardness.

Figure 11:
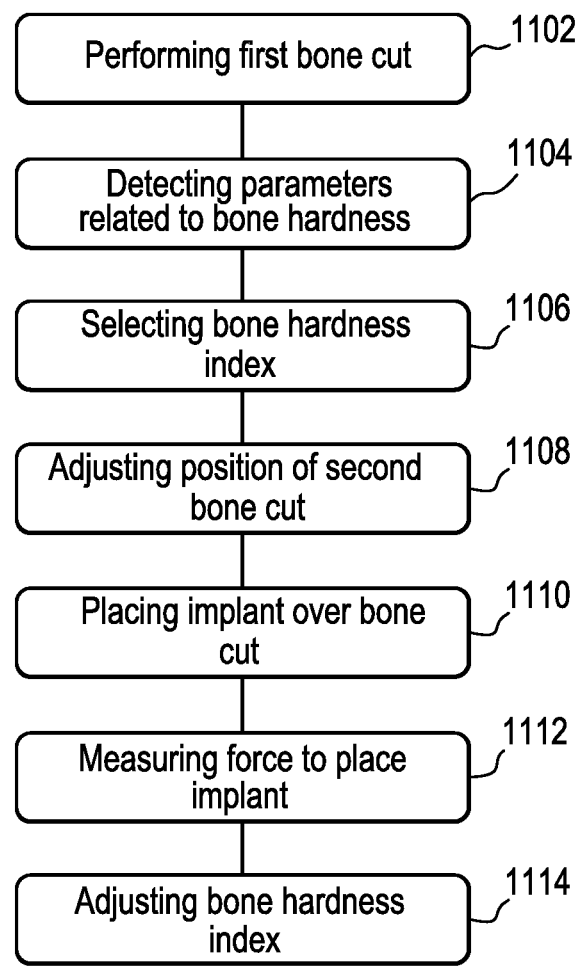
FIG. 11 is a flowchart of another embodiment of a method of adjusting bone cut positioning including adjusting a bone hardness index based on force required to place an implant.

In addition to user correction mentioned above, certain embodiments can include other procedures for verifying and refining accuracy of the empirical models or algorithms utilized to relate detected parameters related to bone hardness to particular bone hardness index values. In one example method illustrated in FIG. 11, a force required to place an implant can be monitored to determine if the selected bone hardness index value was appropriate. For example, the method can proceed as outlined in one of the embodiments above to select a bone hardness index and adjust a position of a second bone cut (e.g., any of an anterior and a posterior femur cut in a knee arthroplasty procedure). The method can further include placing an implant over the areas of the first and second bone cuts (1110) and measuring a force required place the implant (1112). Based on the measured force, the method can include adjusting a bone hardness index (1114) or adjusting the underlying empirical model or algorithm that related the detected parameters related to bone hardness with the particular bone hardness index value.

The energy required to place the implant can be recorded either by the CAS system (e.g., by a robot used to place the implant) or by using a separate and/or external tool configured to measure implant placement force. If utilizing a robot for placement, the above-described methods of recording total energy (e.g., work) consumption or instantaneous energy (e.g., force) consumption over time required by the robot can be utilized to measure implanting force. The gathered information on implanting force can be utilized in the same manner as the above-described user correction to check if the A-P distance calculated and executed by the CAS system based on the detected parameters and selected bone hardness index was appropriate. Such a measurement can replace or complement a surgeon's judgement on the hardness index determined by the system. Further, any correction based on this data can be fed into the expert system, empirical model, or algorithm to improve performance in determining bone hardness index values.

Figure 12:
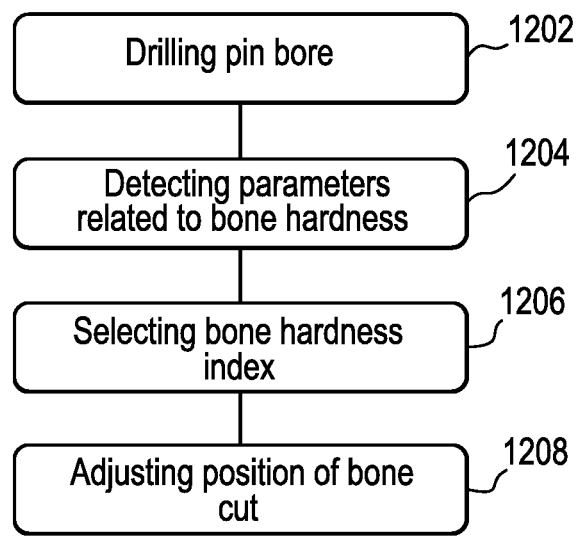
FIG. 12 is a flowchart of another embodiment of a method of adjusting bone cut positioning including drilling a pin bore.

In some embodiments, the systems and methods disclosed herein can detect one or more parameters related to bone hardness before performing a first bone cut. As shown in FIG. 12, for example, in some embodiments a method according to the present disclosure can include drilling at least one pin bore (1202) in bone, detecting one or more parameters related to bone hardness (1204), selecting a bone hardness index based on the one or more parameters related to bone hardness (1206), and adjusting a position of a bone cut (1208). By way of further example, in some embodiments an at least partially robot-assisted surgical drill can be utilized to drill a pin bore in a patient's femur prior to making either the anterior or posterior femur cuts. As with the examples described above, detecting one or more parameters related to bone hardness can include recording total energy required by the surgical drill to form the pin bore. And similar to the examples above, the internal energy consumption of the surgical drill can be subtracted.

In other embodiments, detecting one or more parameters related to bone hardness can include recording instantaneous energy required by the surgical drill to form the pin bore (as noted above, internal energy consumption of the drill can be subtracted). In such an embodiment, detecting one or more parameters related to bone hardness can further include correlating the recorded instantaneous energy required at each time while forming the pin bore with a position of the surgical drill to map variations in bone hardness over a depth of the pin bore. Such a method can allow analysis for non-homogeneity of bone hardness and can allow the bone hardness index to be selected based on bone hardness data for select portions of bone. For example, bone hardness parameters related to areas known to contain cortical bone can be ignored when selecting a bone hardness index in some embodiments.

The method illustrated in FIG. 12 can be advantageous in that some CAS Systems require a surgeon to drill pins into the bones as part of a typical setup for the procedure prior to executing the bone cuts, e.g. to attach an array used for bone tracking, etc. These pins can be Schanz screws in some embodiments. Similar to the above described embodiments, the energy required to place a pin can increase with bone hardness. Accordingly, an empirical model can similarly determine a bone hardness index based on the energy required to place the pin.

Figure 13:
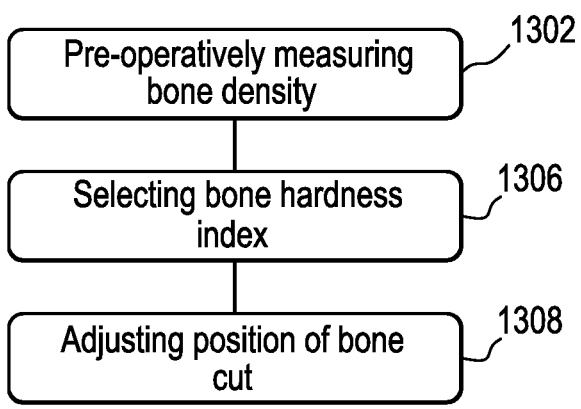
FIG. 13 is a flowchart of another embodiment of a method of adjusting bone cut positioning including pre-operatively measuring bone density.

FIG. 13 illustrates another embodiment wherein detecting one or more parameters related to bone hardness is performed prior to performing any bone cut. More particularly, the method can include pre-operatively measuring bone density (1302), selecting a bone hardness index (1306) based on the pre-operative measurement of bone density, and adjusting a position of a bone cut (1308). Any of a variety of pre-operative bone density measurement techniques can be utilized, including quantitative computed tomography (QCT), dual energy x-ray absorptiometry (DEXA), and biopsy, among others. Results of the pre-operative measurement can be related to a bone hardness index via an empirical model or algorithm, in a similar manner as described above.

A method involving a pre-operative assessment of bone density can be advantageous in certain situations, e.g., when designing patient-specific instrumentation (e.g., cutting blocks, etc.) ahead of a procedure, or when selecting single-use instrumentation. For example, if utilizing cutting blocks for form the anterior and posterior femur cuts in a knee arthroplasty procedure, for example, different cutting blocks can be manufactured for each implant size and the cutting blocks can have different A-P distances that match with different bone hardness index values. Accordingly, the most appropriate cutting block can be selected given an implant size and selected bone hardness index based on the pre-operative measurement of bone density. Such methods can also be advantageous when utilizing a CAS system that requires pre-operative planning, which is often the case with image-based CAS systems.

As noted above, the systems and methods disclosed herein can also provide advantages in improving the precision and accuracy of bone cuts performed with robot assistance or control. For example, in embodiments utilizing oscillating blade cutting tools, variations in bone density can affect both the vertical and horizontal oscillating movements, i.e., the saw kerf created during a cut can increase as bone density decreases because the saw vibrates more in softer bone and therefore removes more bone. Furthermore, more dense or harder bone can cause saw cuts to curve over their length (e.g., a plane of a cut ends up angled such that it is deeper at its beginning than its end even if intended to remain flat). The systems and methods described herein can provide opportunities to compensate for these effects based on the selected bone hardness index. For example, placement of a cut could be adjusted to account for a larger kerf with less dense bone (or a smaller kerf with more dense bone), or a path of a saw could be curved in a manner to counter the shallowing curve typically caused by more dense bone. As a result, the systems and methods described herein can help improve bone cut precision and accuracy by reducing or at least accounting for increased saw vibration and producing more planar bone cuts.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The systems and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

One skilled in the art will appreciate further features and advantages based on the above-described embodiments. Accordingly, the disclosure is not to be limited by what has been particularly shown and described. All publications and references cited herein are expressly incorporated herein by reference in their entirety.

What is claimed is:

1. A surgical method for adjusting bone cut positioning, comprising:
performing a first bone cut of a bone for receiving an implant using an at least partially robot-assisted surgical instrument;
determining an energy consumed by the surgical instrument to perform the first bone cut;
correlating the determined energy to one or more predetermined parameters related to bone hardness;
assigning a bone hardness index to the bone based on the one or more predetermined parameters, wherein a higher bone hardness index indicates a relatively harder bone and a lower bone hardness index indicates a relatively softer bone; and
planning a position of a second bone cut of the bone distinct from the first bone cut based on the assigned bone hardness index, wherein, if the bone has a higher assigned bone hardness index, a greater amount of the bone is removed than if the bone had a lower assigned bone hardness index.

2. The method of claim 1, wherein the first bone cut is a distal cut of a femur during a knee arthroplasty operation.

3. The method of claim 2, wherein the second bone cut is any of an anterior and a posterior cut of the femur.

4. The method of claim 1, further comprising placing the implant over the areas of the first and second bone cuts.

5. The method of claim 4, wherein the implant is a cementless, press-fit implant.

6. The method of claim 4, further comprising measuring a force required to place the implant; and adjusting the bone hardness index based the measured force.

7. The method of claim 1, wherein the first bone cut creates or enlarges a cavity in the bone.

8. The method of claim 7, wherein the bone is a pelvis.

9. The method of claim 8, wherein the cavity is an acetabulum.

10. The method of claim 7, wherein the second bone cut is a final bone cut that determines a surface configured to contact the implant.

11. The method of claim 10, wherein the implant is a cementless, press-fit implant.

12. The method of claim 1, further comprising receiving from a user a correction to the bone hardness index.

13. The method of claim 1, wherein correlating the determined energy to the one or more parameters related to bone hardness occurs while performing the first bone cut.

14. The method of claim 13, wherein correlating the determined energy to the one or more parameters related to bone hardness includes recording total energy required by the surgical instrument to perform the first bone cut relative to an area of the first bone cut.

15. The method of claim 13, wherein correlating the determined energy to the one or more parameters related to bone hardness includes continuously recording instantaneous energy required by the surgical instrument to perform the first bone cut.

16. The method of claim 15, wherein correlating the determined energy to the one or more parameters related to bone hardness further includes correlating the recorded instantaneous energy required at each time during the first bone cut with a position of the surgical instrument to map variations in bone hardness over an area of the first bone cut.

17. The method of claim 16, wherein the bone hardness index is assigned based on discarding recorded bone hardness information for select area of the first bone cut.

18. The method of claim 17, wherein the select area of the first bone cut includes cortical bone area.

19. The method of claim 1, further comprising utilizing a robot to advance an instrument into bone exposed by the first bone cut in a direction transverse to a plane of the first bone cut.

20. The method of claim 19, further comprising recording total energy required by the robot to advance the instrument.

21. The method of claim 19, further comprising continuously recording instantaneous energy required by the robot to advance the instrument.

22. The method of claim 19, wherein the instrument advanced into the bone is any of the surgical instrument utilized to perform the first bone cut, a surgical drill, a pin, and another surgical instrument.

23. The method of claim 1, further comprising drilling at least one pin bore using an at least partially robot-assisted surgical drill.

24. The method of claim 23, further comprising recording total energy required by the surgical drill to form the at least one pin bore.

25. The method of claim 23, further comprising continuously recording instantaneous energy required by the surgical drill to form the at least one pin bore.

26. The method of claim 25, further comprising correlating the recorded instantaneous energy required at each time while forming the at least one pin bore with a position of the surgical drill to map variations in bone hardness over a depth of the at least one pin bore.

27. The method of claim 26, wherein the bone hardness index is assigned based on discarding recorded bone hardness information for select portions of the at least one pin bore.

28. The method of claim 27, wherein the select portions of the at least one pin bore include cortical bone portions.

29. A surgical method, comprising:
performing a first bone cut on a bone for receiving an implant using an at least partially robot-assisted surgical instrument;
determining an energy consumed by the surgical instrument to perform the first bone cut;
correlating the determined energy to a predetermined parameters related to hardness of the bone;
assigning a bone hardness index value to the bone, wherein a higher bone hardness index indicates a relatively harder bone and a lower bone hardness index indicates a relatively softer bone; and
planning a position of a second bone cut on the bone, wherein the first bone cut and the second bone cut are spaced a distance apart, the distance being based on the bone hardness index value, wherein, if the bone has a higher assigned bone hardness index, the distance is less than if the bone had a lower assigned bone hardness index.

30. The method of claim 29, further comprising at least one of drilling a pin bore in the bone or advancing an instrument into the bone, determining a work performed or a force exerted, and using the determined work or force in the correlation of the bone hardness.

31. The method of claim 29, wherein correlating the determined energy to the hardness of the bone further comprises receiving a correction to the bone hardness determination from a user and adjusting the position of the second bone cut on the bone relative to the planned position of the second bone cut based on the corrected bone hardness.

32. The method of claim 1, wherein planning the position of the second bone cut on the bone further comprises accounting for a blade deflection associated with cutting bone of the bone hardness index.

33. The method of claim 29, wherein planning the position of the second bone cut on the bone further comprises accounting for a blade deflection associated with cutting bone of the bone hardness.

* * * * *